United States Patent [19]
Fleisch et al.

[11] Patent Number: 5,914,340
[45] Date of Patent: *Jun. 22, 1999

[54] LEUKOTRIENE ANTAGONISTS USEFUL FOR TREATING DERMATOSES

[75] Inventors: Jerome H. Fleisch, Carmel; William T. Jackson; Jason S. Sawyer, both of Indianapolis, all of Ind.

[73] Assignee: Eli Lilly and Company, Indianapolis, Ind.

[21] Appl. No.: 09/039,027

[22] Filed: Mar. 13, 1998

Related U.S. Application Data

[60] Provisional application No. 60/041,569, Mar. 21, 1997.

[51] Int. Cl.$^6$ .......................... A61K 31/19; C07D 257/04
[52] U.S. Cl. .............................. 514/381; 514/13; 514/14; 514/15; 514/16; 514/17; 514/18; 514/19; 514/252; 514/318; 514/332; 514/340; 514/343; 514/346; 514/347; 514/351; 514/521; 514/520; 514/570; 514/239.5; 514/239.2; 514/238.8; 514/237.8; 514/233.5; 514/232.8
[58] Field of Search ................................ 514/381, 13, 14, 514/15, 16, 17, 18, 19, 235, 252, 318, 332, 340, 343, 346, 347, 351, 520, 521, 570, 571

[56] References Cited

U.S. PATENT DOCUMENTS

| | | | |
|---|---|---|---|
| 4,885,309 | 12/1989 | Welton | 514/456 |
| 5,001,136 | 3/1991 | Walker | 514/336 |
| 5,462,954 | 10/1995 | Baker et al. | 514/381 |

OTHER PUBLICATIONS

Fogh, et al., *J. Allergy Clin. Immunol.*, 83: 450–455 (1989).
Barr, et al., *British Journal of Dermatology*, III: 23–28 (1984).
Czaretzki, *Clin. Exp. Immunol.*, 54: 486–492 (1983).
Rosenbach, et al., *British Journal of Dermatology*, 113: Supplement 28: 157–167 (1985).
Sawyer, J. Scott, *Exp. Opin. Invest. Drugs* 5(1) :73–77 (1996).
Sawyer, J. Scott, *Drugs of the Future*, 21 (6):610–614 (1996).

*Primary Examiner*—James H. Reamer
*Attorney, Agent, or Firm*—Nelsen L. Lentz

[57] ABSTRACT

This invention provides methods for the treatment or inhibiting of dermatitis which comprises administering to a mammal in need thereof an effective amount of a compound having activity as a leukotriene $B_4$ antagonist.

9 Claims, No Drawings

LEUKOTRIENE ANTAGONISTS USEFUL FOR TREATING DERMATOSES

This Application claims the benefit of U.S. Provisional Patent Application Ser. No. 60/041,569 filed Mar. 21, 1997.

BACKGROUND OF THE INVENTION

Dermatoses produce a great burden of suffering on the afflicted. The number of inflammatory or allergic dermatoses is continuously increasing, especially in the industrialized countries. Common manifestations of dermatoses include contact dermatitis and atopic dermatitis.

Contact dermatitis is an acute or chronic inflammation, often sharply demarcated, produced by substances in contact with the skin. Contact dermatitis may be caused by a primary chemical irritant or may be a delayed hypersensitivity reaction. Contact dermatitis ranges from transient redness to severe swelling with bulla formation; itching and vesiculation are common. Any exposed skin surface that contacts a sensitizing or irritating substance may be involved. Thus, dermatitis may be due to an airborne substance (e.g., ragweed pollen, insecticide spray). Typically, the dermatitis is first sharply limited to the site of contact; later it may spread.

Products for the treatment of these disorders include antihistaminics or glucocorticoids. For prophylaxis, on the other hand, no suitable preparations are known. Unless the offending agent is removed, treatment may be ineffective or the dermatitis may promptly recur. Patients with photoallergic or phototoxic contact dermatitis should also avoid exposure to light. Antihistamines (except for their sedative effect) and allergen desensitization are ineffective in contact dermatitis.

Atopic dermatitis is a chronic, itching, superficial inflammation of the skin, frequently associated with a personal or family history of related disorders (e.g., hay fever, asthma). Atopic dermatitis is a chronic inflammatory skin disorder. According to data from a national screening survey of dermatologic disease, the prevalence of atopic dermatitis among persons one year to 74 years of age ranges form seven to 24 cases per 1,000.

Atopic dermatitis is most prevalent in infancy and childhood and tends to be less prevalent during puberty; however, the condition often persists into adulthood, and in a small number of cases (fewer than two percent), onset occurs in persons order than 45 years. Atopic dermatitis is not a primary allergic disorder per se but appears to be inherited in association with certain allergic disorders. Environmental stimuli can trigger the disease in genetically predisposed individuals.

The increased prevalence of atopic dermatitis in the 1990s has been attributed to environmental irritants, infections, previous exposure to allergenic foods, and airborne allergens such as dust, mites, animal dander, and pollens.

Atopy is characterized by physiologic, immunopathologic, and pharmacological abnormalities that involve the skin. These abnormalities include (1) a lowered threshold to itch stimuli, (2) a hypersensitivity to alpha-adrenergic agonists and to cholinergic agents, which may result from partial beta-adrenergic blockade, (3) a very dry (xerotic), hyperkeratotic skin, which has decreased water-holding capacity, (4) a marked tendency to produce lichenification in response to friction and scratching, and (5) a tendency for the skin to be heavily colonized with bacteria, especially pathogenic staphylococci.

Itching is the primary symptom of atopic dermatitis. The pruritus may be generalized or localized, especially to the flexor surfaces. It fluctuates seasonally, is often worse in the wintertime, and has a diurnal rhythm in which itching is minimal at midday and maximal in the evening. Higher body temperature and capillary dilatation in the evening and the absence of daytime distractions account for the diurnal cycle. Emotional stress can also provoke and aggravate itching and scratching.

The diagnosis of atopic dermatitis is usually clinically evident; histologic examination reveals a nonspecific eczematous process. Patients commonly have a history of dermatitis in infancy and a family or personal history of atopy. Eczema connotes a reaction pattern of the skin to multiple exogenous and endogenous stimuli that is characteristic of a particular type of dermatitis. At some stage of the eczematous process, small, often microscopic, blisters or vesicles from within the epidermis because of accumulation of intercellular fluid, also called spongiosis.

The objectives of local therapy for atopic dermatitis are suppression of inflammation, hydration of the skin, reduction of skin bacteria, and prevention of itching and scratching. Itching leads to scratching and to trauma of the skin, resulting in infection, lichenification, and eczematization.

Anti-inflammatory and antipuritic agents include topical corticosteroids of varying potencies and purified coal tar derivatives such as five percent liquor carbonis detergens (LCD) in a propylene glycol or cream base.

However, these therapies, have some disadvantages; in many people, some antihistaminics cause languor and drowsiness. Permanent use of glucocorticoids (for example cortisone) is usually unjustifiable for medical reasons owing to many unpleasant side effects. The same also applies to most so-called NSAID (non-steroidal anti-inflammatory drugs).

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A) and have been designated leukotrienes $C_4$, $D_4$, and $E_4$ ($LTC_4$, $LTD_4$, and $LTE_4$, respectively).

Another arachidonic acid metabolite, leukotriene $B_4$ ($LTB_4$), is a proinflammatory lipid which has been implicated in the pathogenesis of psoriasis, arthritis, chronic lung diseases, acute respiratory distress syndrome, shock, asthma, inflammatory bowel diseases, and other inflammatory states characterized by the infiltration and activation of polymorphonuclear leukocytes and other proinflammatory cells. Thus activated, the polymorphonuclear leukocytes liberate tissue-degrading enzymes and reactive chemicals causing the inflammation. Antagonism of $LTB_4$ should therefore provide a novel therapeutic approach to treatment of these and other $LTB_4$ mediated conditions. Activated microglial cells are the central nervous system analogues of systemic proinflammatory cells.

Because of the debilitating effects of dermatoses there continues to exist a need for effective treatments.

SUMMARY OF THE INVENTION

This invention provides a method for the treatment or inhibiting of dermatoses in mammals comprising administering to a mammal in need thereof an effective amount of a compound of Formula I

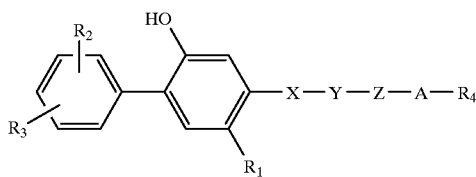

wherein:

R$_1$ is C$_1$–C$_5$ alkyl, C$_2$–C$_5$ alkenyl, C$_2$–C$_5$ alkynyl, C$_1$–C$_4$ alkoxy, (C$_1$–C$_4$ alkyl)thio, halo, or R$_2$-substituted phenyl;

each R$_2$ and R$_3$ are each independently hydrogen, halo, hydroxy, C$_1$–C$_4$ alkyl, C$_1$–C$_4$ alkoxy, (C$_1$–C$_4$ alkyl)—S(O)$_q$—, trifluoromethyl, or di-(C$_1$–C$_3$ alkyl)amino;

X is —O—, —S—, —C(=O), or —CH$_2$—;

Y is —O— or —CH$_2$—;

or when taken together, —X—Y— is —CH=CH— or

—C≡C—;

Z is a straight or branched chain C$_1$–C$_{10}$ alkylidenyl;

A is a bond, —O—, —S—, —CH=CH—, or —CR$_a$R$_b$—, where R$_a$ and R$_b$ are each independently hydrogen, C$_1$–C$_5$ alkyl, or R$_7$-substituted phenyl, or when taken together with the carbon atom to which they are attached form a C$_4$–C$_8$ cycloalkyl ring;

R$_4$ is R$_6$,

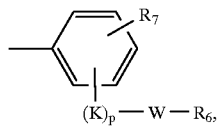

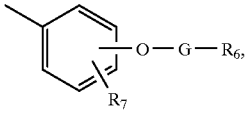

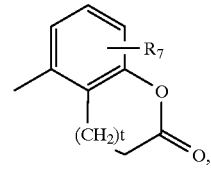

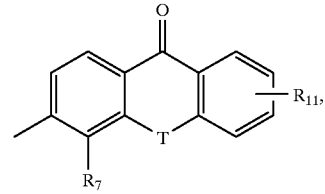

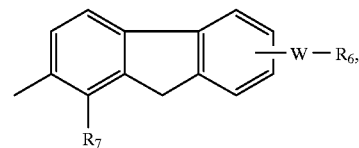

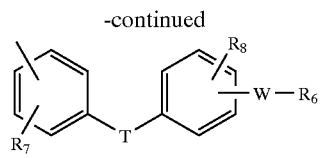

where, each R$_6$ is independently —COOH, 5-tetrazolyl, —CON(R$_9$)$_2$, or —CONHSO$_2$R$_{10}$;

each R$_7$ is hydrogen, C$_1$–C$_4$ alkyl, C$_2$–C$_5$ alkenyl, C$_2$–C$_5$ alkynyl, benzyl, methoxy, —W—R$_6$, —T—G—R$_6$, (C$_1$–C$_4$ alkyl)—T—(C$_1$–C$_4$ alkylidenyl)—O—, or hydroxy;

R$_8$ is hydrogen or halo;

each R$_9$ is independently hydrogen, phenyl, or C$_1$–C$_4$ alkyl, or when taken together with the nitrogen atom form a morpholino, piperidino, piperazino, or pyrrolidino group;

R$_{10}$ is C$_1$–C$_4$ alkyl or phenyl;

R$_{11}$ is R$_2$, —W—R$_6$, or —T—G—R$_6$;

each W is a bond or straight or branched chain divalent hydrocarbyl radical of one to eight carbon atoms;

each G is a straight or branched chain divalent hydrocarbyl radical of one to eight carbon atoms;

each T is a bond, —CH$_2$—, —O—, —NH—, —NHCO—, —C(=O)—, or —S(O)$_q$—;

K is —C(=O)— or —CH(OH)—;

each q is independently 0, 1, or 2;

p is 0 or 1; and t is 0 or 1;

provided when X is —O— or —S—, Y is not —O—;

provided when A is —O— or —S—, R$_4$ is not R$_6$;

provided when A is —O— or —S— and Z is a bond, Y is not —O—; and provided W is not a bond when p is 0;

or a pharmaceutically acceptable salt or solvate thereof.

DETAILED DESCRIPTION

The following definitions refer to the various terms used throughout this disclosure.

The term "C$_1$–C$_5$ alkyl" refers to the straight and branched aliphatic radicals of 1 to 5 carbon atoms such as methyl, ethyl, propyl, isopropyl, n-butyl, sec-butyl, tert-butyl, n-pentyl, 2,2-dimethylpropyl, and the like. Included within this definition are the terms "C$_1$–C$_3$ alkyl" and "C$_1$–C$_4$ alkyl".

The term "C$_2$–C$_5$ alkenyl" refers to straight and branched aliphatic radicals of 2 to 5 carbon atoms containing one double bond, such as —CH=CH—, —CH$_2$CH=CH$_2$, —CH$_2$CH$_2$CH=CH$_2$, —CH$_2$C(CH$_3$)=CH$_2$, —CH$_2$CH=C(CH$_3$)$_2$, and the like.

The term "C$_2$–C$_5$ alkynyl" refers to straight and branched aliphatic residues of 2 to 5 carbon atoms containing one triple bond, such as —C≡CH, —CH$_2$—C≡CH, —CH$_2$CH$_2$C≡CH, —CH$_2$CH(CH$_3$)C≡CH, —CH$_2$C≡CCH$_3$, and the like.

The term "C$_1$–C$_4$ alkoxy" refers to methoxy, ethoxy, propoxy, isopropoxy, butoxy, sec-butoxy, and tert-butoxy.

The term "halo" refers to fluoro, chloro, bromo, and iodo.

The term "C$_1$–C$_{10}$ alkylidenyl" refers to a divalent radical derived from a C$_1$–C$_{10}$ alkane such as —CH$_2$—, —CH (CH₃)—, —C(CH₃)₂—, —CH(C₂H₅)—, —CH₂CH₂—, —CH₂CH(CH₃)—, —CH(CH₃)CH₂—, —CH(CH₃)CH (CH₃)—, —CH₂C(CH₃)₂—, —CH₂CH(C₂H₅)—, —CH₂CH₂CH₂—, —CH(CH₃)CH₂CH₂—, —CH₂CH (CH₃)CH₂—, —CH₂CH(C₂H₅)CH₂—, —CH₂CH₂CH (C₂H₅)—, —C(CH₃)₂CH₂CH₂—, —CH(CH₃)CH₂CH (CH₃)—, —CH₂CH₂CH₂CH₂—, —CH₂C(CH₃) ₂CH₂CH₂—, —CH₂C(CH₃)₂CH₂—, —CH₂CH₂CH(C₂H₅) CH₂—, CH₂CH₂CH₂CH₂CH₂—, —CH(CH₃) CH₂CH₂CH₂CH₂—, —CH₂CH₂CH₂CH₂CH₂CH₂—, —(CH₂)₁₀—, and the like. Included within this definition are the terms "C₁–C₄ alkylidene" and "C₂–C₄ alkylidene".

The term "C₄–C₈ cycloalkyl" refers to a cycloalkyl ring of four to eight carbon atoms, such as cyclobutyl, cyclopentyl, cyclohexyl, 4,4-dimethylcyclohexyl, cycloheptyl, cyclooctyl, and the like.

The term "straight or branched chain divalent hydrocarbyl residue of one to eight carbon atoms" refers to a divalent radical derived from a straight or branched alkane, alkene, or alkyne of one to eight carbon atoms. Depending upon the branching and number of carbon atoms, as will be appreciated by organic chemists, such a moiety can contain one, two or three double or triple bonds, or combinations of both. As such, this term can be considered an alkylidene group as defined above containing from 1 to 8 carbon atoms optionally containing one to three double or triple bonds, or combinations of the two, limited as noted in the preceding sentence.

This invention includes the pharmaceutically acceptable base addition salts of the compounds of Formula I. Such salts include those derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred.

This invention includes both mono-salt forms, i.e., a 1:1 ratio of a compound of Formula I with a base as previously described, as well as di-salt forms in those instances where a compound of Formula I has two acidic groups. In addition, this invention includes any solvate forms of the compounds of Formula I or salts thereof, such as ethanol solvates, hydrates, and the like.

It is recognized that in compounds having branched alkyl, alkylidenyl, or hydrocarbyl functionality, and in those compounds bearing double or triple bonds, various stereoisomeric products may exist. This invention is not limited to any particular stereoisomer but includes all possible individual isomers and mixtures thereof. The term "5-tetrazolyl" refers to both tautomers, ie, (1H)-5-tetrazolyl and (2H)-5-tetrazolyl.

PREFERRED EMBODIMENTS

A most preferred group of compounds employed in the methods of the present invention are those compounds of Formula Ia:

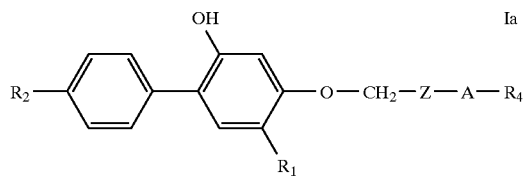

and pharmaceutically acceptable base addition salts thereof. Especially preferred are those compounds wherein R₂ is halo, particularly fluoro. Preferred R₁ substituents are propyl and especially ethyl.

Preferred Z substituents include C₂–C₄ alkylidene, particularly —CH₂CH₂— and —CH₂CH₂CH₂CH₂—. Preferred A groups include —O—, —CH₂—, —CH(R₇-substituted phenyl)—, and —C(CH₃)₂.

Preferred R₄ groups include —COOH, 5-tetrazolyl, or a mono-, di-, or tri-cyclic group as drawn above wherein there is at least one acidic group attached to a ring, such as —W—COOH, —T—C—COOH, or the corresponding tetrazole derivatives. The preferred W moiety is that of a bond or straight chain C₁–C₄ alkylidene; preferred G moieties are straight chain C₁–C₄ alkylidene. It is preferred that R₅ or R₇ be C₁–C₄ alkyl, especially n-propyl.

Particularly preferred groups are those wherein A is —CH(R₇—substituted phenyl)- and R₄ is —COOH or 5-tetrazolyl. Also preferred are those compounds wherein A is —O— and R₄ is

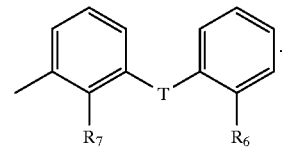

Preferred aspects of this substructure are those wherein R₇ is C₁–C₄ alkyl, especially n-propyl, and R₆ is —W—COOH. Particularly preferred are those compounds wherein T is —O— or —S— and W is a bond.

Particularly preferred compounds of the instant invention include 2-[2-propyl-3-[3-[2-ethyl-4-(4-fluorophenyl)-5-hydroxyphenoxy]propoxy]phenoxy]benzoic acid; 3-(2-(3-(2-ethyl-4-(4-fluorophenyl)-5-hydroxyphenoxy)propoxy)-6-(4-carboxy-phenoxy)phenyl)propionic acid; 1-(4-(carboxy-methoxy)phenyl)-1-(1H-tetrazol-5-yl)-6-(2-ethyl-4-(4-fluorophenyl)-5-hydroxyphenoxy)hexane ; 3-[4-[7-carboxy-9-oxo-3-[3-[2-ethyl-4-(4-fluorophenyl)-5-hydroxyphenoxy]-propoxy]-9H-xanthene]]propanoic acid and 5-[3-[2-(1-carboxy)-ethyl]-4-[3-[2-ethyl-4-(4-fluorophenyl)-5-hydroxyphenoxy]-propoxy]phenyl]-4-pentynoic acid or a pharmaceutically acceptable salt or solvate thereof.

The leukotriene B₄ (LTB₄) antagonists employed in the methods of the present invention may be synthesized essentially as described in U.S. Pat. No. 5,462,954 issued Oct. 31, 1995, the entire contents of which are herein incorporated by reference.

The following examples further illustrate the preparation of the intermediates and compounds of this invention. The examples are illustrative only and are not intended to limit the scope of the invention. Melting points were determined on a Thomas-Hoover apparatus and are uncorrected. NMR spectra were determined on a GE QE-300 spectrometer. All chemical shifts are reported in parts per million (__) relative to tetramethylsilane. Chemical shifts of aromatic protons of quinoline species in DMSO-$d_6$ are concentration dependent. The following abbreviations are used to denote signal patterns: s=singlet, d=doublet, t=triplet, q=quartet, b=broad, m=multiplet. Infrared spectra were determined on a Nicolet DX10 FT-IR spectrometer. Mass spectral data were determined on a CEC-21-110 spectrometer using electron impact (EI) conditions, a MAT-731 spectrometer using free desorption (FD) conditions, or a VG ZAB-3F spectrometer using fast atom bombardment (FAB) conditions. Silica gel chromatography was performed using ethyl acetate/hexane gradients unless otherwise indicated. Reverse-phase chromatography was performed on MCI CHP20P gel using an acetonitrile/water or methanol/water gradient unless otherwise indicated. Tetrahydrofuran (THF) was distilled from sodium/benzophenone ketyl immediately prior to use. All reactions were conducted under argon atmosphere with stirring unless otherwise noted. Where structures were confirmed by infra-red, proton nuclear magnetic resonance, or mass spectral analysis, the compound is so designated by "IR", "NMR", or "MS", respectively.

EXAMPLE 1
3-[2-[3-[(5-Ethyl-2-hydroxy[1,1'-biphenyl]-4-yl)oxy]propoxy]-1-dibenzofuran]propanoic acid disodium salt A. Preparation of 3,3-diethoxy-2,3-dihydro-1H-benzofuro-[3,2-f][1]benzopyran.

A solution of 2-hydroxydibenzofuran (5.00 g, 27.2 mmol), triethylorthoacrylate (10.1 g, 54.3 mmol) and pivalic acid (1.39 g, 13.6 mmol) in toluene (100 mL) was refluxed for 18 hours. The mixture was cooled to room temperature and washed once with water and once with a saturated sodium bicarbonate solution, dried over sodium sulfate, filtered and concentrated in vacuo to provide an orange oil. This material was diluted with hexane and maintained at −20° C. for 18 hours. The resulting crystals were collected via vacuum filtration to provide 5.67 g (67%) of the desired title intermediate, mp 64° C.; NMR (CDCl$_3$) 7.96 (d, J=7.8 Hz, 1H), 7.57 (d, J=8.0 Hz, 1H), 7.46 (t, J=8 Hz, 1H), 7.35 (m, 2H), 7.06 (d, J=8.8 Hz, 1H), 3.82 (q, J=7.2 Hz, 2H), 3.73 (q, J=6.8 Hz, 2H), 3.35 (t, J=6.9 Hz, 2H), 2.29 (t, J=7.0 Hz, 2H), 1.23 (t, J=7.1 Hz, 6H); MS-FD m/e 312 (p); IR (CHCl$_3$, cm$^{-1}$) 2982, 1494, 1476, 1451, 1434, 1251, 1090, 1054, 975.

Analysis for $C_{19}H_{20}O_4$:
Calc: C, 73.06; H, 6.45;
Found: C, 72.81; H, 6.72.

B. Preparation of 3-[1-(2-hydroxydibenzofuran)]-propanoic acid ethyl ester.

A mixture of 3,3-diethoxy-2,3-dihydro-1H-benzofuro-[3,2-f][1]benzopyran (3.50 g, 11.2 mmol) and 10% aqueous hydrochloric acid (5 mL) in ethyl acetate (30 mL) was stirred at room temperature for 1 hour. The resulting mixture was washed once with water, dried over sodium sulfate, filtered and concentrated in vacuo to provide a tan solid. Recrystallization from hexane/ethyl acetate provided 3.11 g (98%) of the desired title intermediate as an off-white

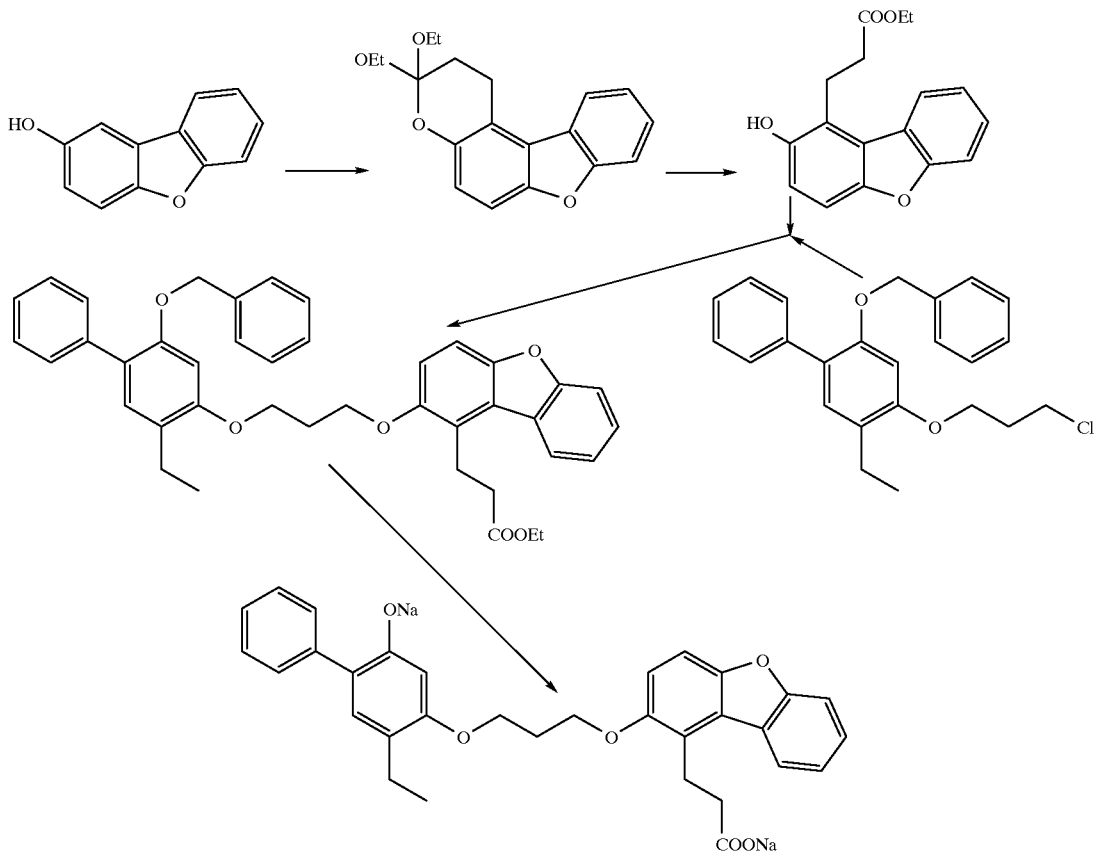

crystalline material: mp 128–131° C.; NMR (CDCl$_3$) 7.88 (d, J=7.7 Hz, 1H), 7.59 (d, J=8.4 Hz, 1H), 7.47 (t, J=7.2 Hz, 1H), 7.37 (d, J=8.9 Hz, 1H), 7.36 (t, J=6.6 Hz, 1H), 7.13 (d, J=8.8 Hz, 1H), 7.13 (q, J=8.8 Hz, 2H), 3.43 (t, J=5.8 Hz, 2H), 3.01 (t, J=7.7 Hz, 2H), 1.23 (t, J=7.2 Hz, 3H); MS-FD m/e 284 (100, p), 256 (65), 238 (17); IR (KBr, cm$^{-1}$) 2985 (b), 1701, 1430, 1226, 1183, 1080.

9

Analysis for $C_{17}H_{16}O_4$:
Calc: C, 71.82; H, 5.67;
Found: C, 71.90; H, 5.43.

C. Preparation of 3-[2-[3-[[5-ethyl-2-(phenylmethoxy)-[1,1'-biphenyl]-4-yl]oxy]propoxy]-1-dibenzofuran]propanoic acid ethyl ester.

3-[1-(2-Hydroxydibenzofuran)]propanoic acid ethyl ester (625 mg, 2.20 mmol) was dissolved in dimethylformamide (10 mL) and carefully treated at room temperature with 95% sodium hydride (58 mg, 2.4 mmol). When gas evolution had ceased, 2-benzyloxy- 1-phenyl-5-ethyl-4-(3-chloro-1-propyloxy)benzene (836 mg, 2.20 mmol) was added and the resulting mixture was stirred for 18 hours. The mixture was diluted with ether and washed once with water. The organic layer was dried over sodium sulfate, filtered, and concentrated in vacuo to provide a dark oil. Silica gel chromatography (ethyl acetate/hexane) provided 200 mg (14%) of the desired titled intermediate as a colorless oil: NMR (CDCl$_3$) 8.11 (d, J=7.7 Hz, 1H), 7.57 (m, 3H), 7.48 (t, J=7.3 Hz, 1H), 7.20–7.44 (m, 10 H), 7.17 (s, 1H), 7.08 (d, J=8.9 Hz, 1H), 6.67 (s, 1H), 5.05 (s, 2H), 4.29 (t, J=6.2 Hz, 2H), 4.26 (t, J=6.1 Hz, 2H), 4.15 (q, J=7.2 Hz, 2H), 3.54 (t, J=8.5 Hz, 2H), 2.67 (m, 4H), 2.37 (t, J=6.0 Hz, 2H), 1.21 (m, 6H).

D. Preparation of 3-[2-[3-[(5-ethyl-2-hydroxy[1,1'-biphenyl]-4-yl)oxy]propoxy]-1-dibenzofuran]propanoic acid disodium salt.

To a nitrogen-purged solution of 3-[2-[3-[[5-ethyl-2-(phenylmethoxy)[1,1'-biphenyl]-4-yl]oxy]propoxy]-1-dibenzofuran]propanoic acid ethyl ester (200 mg, 0.318 mmol) in a 1:1 mixture of methanol/tetrahydrofuran (40 mL) was added 10% palladium on carbon (25 mg). The resulting suspension was hydrogenated at 1 atm pressure for 24 hours at room temperature. The mixture was filtered through a short pad of Florisil® and the filtrate concentrated in vacuo. The residue was dissolved in a 1:1 mixture of methanol/tetrahydrofuran (20 mL) and treated with 5N sodium hydroxide solution (2 mL) at room temperature for 24 hours. The resulting mixture was extracted once with diethyl ether. The aqueous layer was acidified with 5N hydrochloric acid solution and extracted twice with methylene chloride. The combined methylene chloride fractions were concentrated in vacuo. The residue was dissolved in a minimum of 1N sodium hydroxide solution and purified on HP-20 resin to provide 53 mg (30%) of the desired title product as a fluffy white solid: NMR (DMSO-d$_6$) 8.12 (d, J=6.9 Hz, 1H), 7.64 (d, J=8.2 Hz, 1H), 7.37–7.57 (m, 5H), 7.30 (m, 2H), 7.14 (m, 2H), 6.96 (s, 1H), 6.93 (s, 1H), 4.30 (t, J=7.3 Hz, 2H), 4.14 (t, J=5.4 Hz, 2H), 2.48 (m, 4H), 2.23 (m, 4H), 1.10 (t, J=7.6 Hz, 3H); MS-FAB m/e 555 (88, p+1), 533 (62); IR (CHCl$_3$, cm$^{-1}$) 3384 (b), 2969, 1566, 1428, 1257, 1181.

Analysis for $C_{32}H_{28}O_6Na_2$:
Calc: C, 69.31; H, 5.09;
Found: C, 69.51; H, 5.39.

10

EXAMPLE 2

7-Carboxy-9-oxo-3-[3-(2-ethyl-5-hydroxy-4-phenylphenoxy)propoxy]-9H-xanthene-4-propanoic acid disodium salt monohydrate

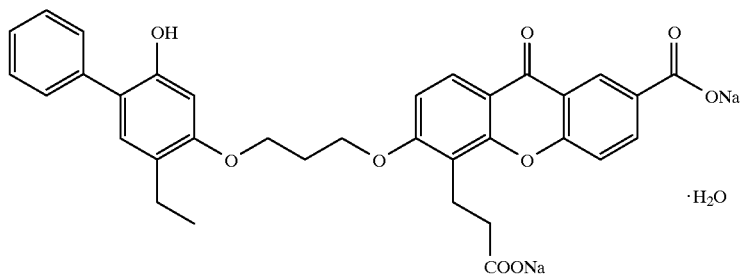

A mixture of 2-benzyloxy-1-phenyl-5-ethyl-4-(3-chloro-1-propyloxy)benzene (749 mg, 1.97 mmol), ethyl 7-carboethoxy-3-hydroxy-9-oxo-9H-xanthene-4-propanoate (729 mg, 1.97 mmol), potassium carbonate (1.36 g, 9.85 mmol) and potassium iodide (33 mg, 0.20 mmol) was refluxed for 24 hours. Dimethylsulfoxide (2 mL) was added and heating continued for 24 hours. The reaction mixture was cooled to room temperature, diluted with ethyl acetate, and washed once with water. The organic layer was dried over sodium sulfate, filtered and concentrated in vacuo to reveal a tan solid. This material was dissolved in ethyl acetate (30 mL) and the resulting solution purged with nitrogen. To this solution was added 10% palladium on carbon (120 mg) and the resulting suspension hydrogenated at 1 atmosphere of pressure. The solution was filtered and concentrated in vacuo to provide a colorless oil. This material was dissolved in a solution of 1:1 methanol/tetrahydrofuran (30 mL) and treated with 5N sodium hydroxide solution (2 mL) at room temperature for 18 hours. The resulting solution was extracted once with diethyl ether and the aqueous layer acidified with 5N hydrochloric acid solution. The resulting precipitate was collected via suction filtration. This material was converted to the di-sodium salt and purified as described above for the preparation of Example 1(D) to provide 390 mg (56%) of the desired title product as a fluffy white solid: NMR (DMSO-d$_6$) 12.65 (s, 1H, —OH), 8.65 (s, 1H), 8.28 (dd, J=8.5, 2.0 Hz, 1H), 8.01 (d, J=8.9 Hz, 1H), 7.50 (m, 3H), 7.29 (t, J=7.8 Hz, 2H), 7.17 (m, 2H), 6.93 (s, 1H, 6.89 (s, 1H), 4.26 (m, 4H), 3.12 (m, 2H), 2.47 (m, 2H), 2.23 (m, 2H), 1.10 (t, J=7.4 Hz, 3H); MS-FAB m/e 627 (24, p), 605 (40), 583 (24), 331 (24), 309 (100); IR (KBr, cm$^{-1}$) 3419 (b), 2962, 1612, 1558, 1443, 1390, 1277, 1084.

Analysis for $C_{34}H_{28}O_9Na_2 \cdot H_2O$:
Calc: C, 63.34; H, 4.69;
Found: C, 63.36; H, 4.50.

EXAMPLE 3

2-[2-Propyl-3-[3-[2-ethyl-4-(4-fluorophenyl)-5-hydroxyphenoxy]propoxy]phenoxy]benzoic acid sodium salt

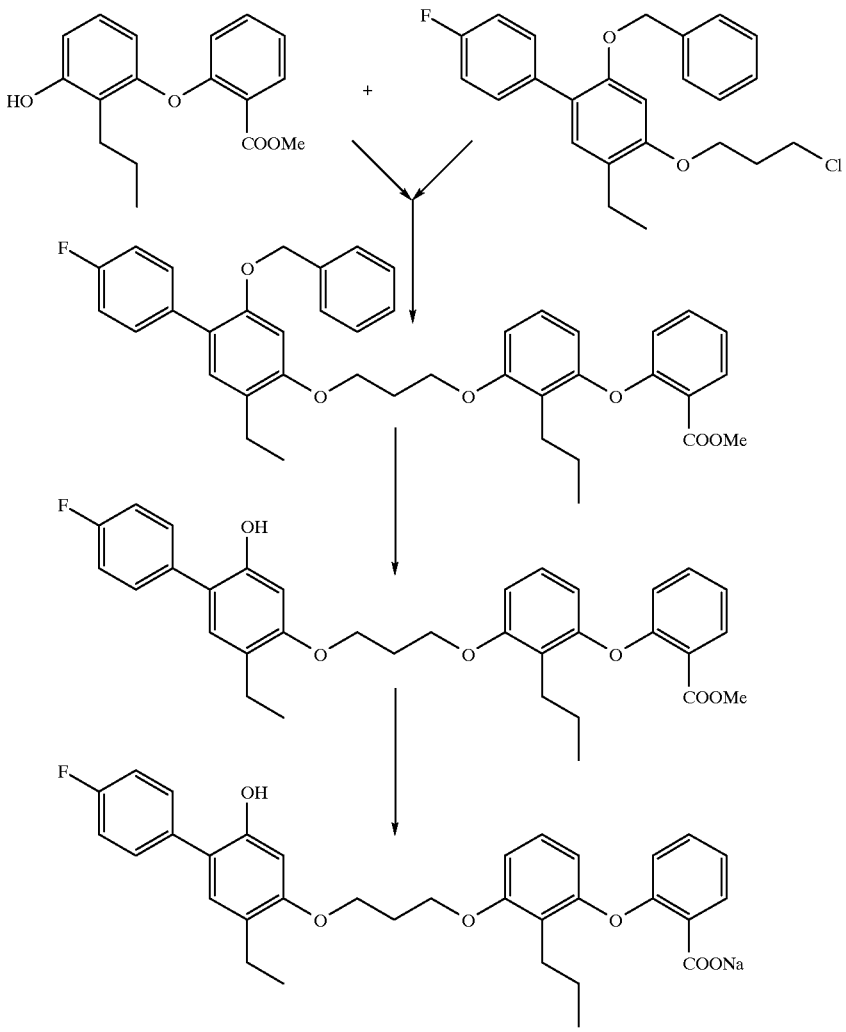

A. Preparation of 2-[2-propyl-3-[3-[2-ethyl-4-(4-fluorophenyl)-5-(phenylmethoxy)phenoxy]propoxy]phenoxy]benzoic acid methyl ester.

A mixture of 2-benzyloxy-1-(4-fluorophenyl)-5-ethyl-4-(3-chloro-1-propyloxy)benzene (20.0 g, 50.2 mmol) and sodium iodide (75.3 g, 502 mmol) in 2-butanone (200 mL) was refluxed for 6 hours. The mixture was diluted with ether and washed once with water. The organic layer was dried over sodium sulfate, filtered, and concentrated in vacuo to provide a colorless oil. This material was dissolved in dimethylformamide (100 mL) and treated with 2-(3-hydroxy-2-propylphenoxy)benzoic acid methyl ester (14.4 g, 50.2 mmol) and potassium carbonate (20.8 g, 151 mmol) at room temperature for 24 hours. This mixture was diluted with water and twice extracted with ether. The aqueous layer was separated and back-extracted once with ethyl acetate. The combined organic layers were dried over sodium sulfate, filtered, and concentrated in vacuo to provide a yellow oil. Silica gel chromatography provided 25.4 g (78%) of the desired title intermediate as a pale golden oil: NMR (CDCl$_3$) 7.91 (d, J=7.8 Hz, 1H), 7.54 (d, J=8.6 Hz, 1H), 7.52 (d, J=8.5 Hz, 1H), 7.25–7.43 (m, 6H), 7.03–7.38 (m, 5H), 6.84 (d, J=8.3 Hz, 1H), 6.71 (d, J=8.1 Hz, 1H), 6.63 (s, 1H), 6.47 (d, J=8.1 Hz, 1H), 5.03 (s, 2H), 4.24 (t, J=5.7 Hz, 2H), 4.21 (t, J=5.8 Hz, 2H), 3.86 (s, 3H), 2.69 (t, J=7.8 Hz, 2H), 2.64 (t, J=7.7 Hz, 2H), 2.34 (quintet, J=6.0 Hz, 2H), 1.60 (hextet, J=5.0 Hz, 2H), 1.22 (t, J=7.5 Hz, 3H), 0.94 (t, J=7.5 Hz, 3H); MS-FD m/e 648 (p); IR (CHCl$_3$, cm$^{-1}$) 2960, 1740, 1604, 1497, 1461, 1112.

Analysis for C$_{41}$H$_{41}$O$_6$F:
Calc: C, 75.91; H, 6.37;
Found: C, 76.15; H, 6.45.

B. Preparation of 2-[2-propyl-3-[3-[2-ethyl-4-(4-fluorophenyl)-5-hydroxyphenoxy]propoxy]phenoxy]benzoic acid methyl ester.

2-[2-Propyl-3-[3-[2-ethyl-4-(4-fluorophenyl)-5-(phenylmethoxy)phenoxy]propoxy]phenoxy]benzoic acid methyl ester (33.0 g, 50.9 mmol) was de-benzylated as described above for the preparation of Example 2 to provide 27.3 g (96%) of the title intermediate as an amber oil: NMR (CDCl$_3$) 7.90 (dd, J=7.8, 1.7 Hz, 1H), 7.42 (m, 3H), 7.05–7.23 (m, 4H), 6.99 (s, 1H), 6.84 (d, J=8.1 Hz, 1H), 6.70 (d, J=8.1 Hz, 1H), 6.55 (s, 1H), 6.46 (d, J=8.1 Hz, 1H), 5.05 (s, 1H, —OH), 4.23 (m, 4H), 3.86 (s, 3H), 2.68 (t, J=7.4 Hz, 2H), 2.62 (q, J=7.5 Hz, 2H), 2.36 (quintet, J=6.0 Hz, 2H), 1.60 (hextet, J=7.7 Hz, 2H), 1.20 (t, J=7.6 Hz, 3H), 0.94 (t, J=7.4 Hz, 3H); MS-FD m/e 558 (p); IR (CHCl$_3$, cm$^{-1}$) 2965, 1727, 1603, 1496, 1458, 1306, 1112.

Analysis for C$_{34}$H$_{35}$O$_6$F:
Calc: C, 73.10; H, 6.31;

Found: C, 73.17; H, 6.42.

C. Preparation of 2-[2-propyl-3-[3-[2-ethyl-4-(4-fluorophenyl)-5-hydroxyphenoxy]propoxy]phenoxy] benzoic acid sodium salt.

2-[2-Propyl-3-[3-[2-ethyl-4-(4-fluorophenyl)-5-hydroxyphenoxy]propoxy]phenoxy]benzoic acid methyl ester (21.5 g, 38.5 mmol) was hydrolyzed as described above for the preparation of Example 2. The acid was converted to the sodium salt and purified as described above for the preparation of Example 1(D) to provide 16.7 g (77%) of the desired title product as a white amorphous solid: NMR (DMSO-$d_6$) 10.50 (bs, 1H, —OH), 7.51 (m, 3H), 7.20 (t, J=7.4 Hz, 1H), 7.13 (m, 2H), 7.00 (m, 2H), 6.95 (s, 1H), 6.67 (dd, J=8.2, 3.3 Hz, 2H), 6.62 (s, 1H), 6.26 (d, J=8.2 Hz, 1H), 4.14 (t, J=5.8 Hz, 2H), 4.02 (t, J=5.7 Hz, 2H), 2.60 (t, J=6.8 Hz, 2H), 2.47 (q, J=7.3 Hz, 2H), 2.16 (t, J=5.9 Hz, 2H), 1.45 (hextet, J=7.5 Hz, 2H), 1.07 (t, J=7.5 Hz, 3H), 0.81 (t, J=7.4 Hz, 3H); MS-FAB m/e 568 (38, p+1), 567 (100, p), 544 (86), 527 (77), 295 (65), 253 (45); IR (KBr, cm$^{-1}$) 3407 (b), 2962, 1603, 1502, 1446, 1395, 1239, 1112.

Analysis for $C_{33}H_{32}O_6FNa$:

Calc: C, 69.95; H, 5.69; F, 3.35;

Found: C, 69.97; H, 5.99; F, 3.52.

The methods of the present invention describe the use of leukotriene antagonists for the treatment or prevention of dematoses which is characterized by the excessive release of leukotriene $B_4$.

The term "excessive release" of a leukotriene refers to an amount of the leukotriene sufficient to cause the symptoms of dermatoses. The amount of leukotriene which is considered to be excessive will depend on a variety of factors, including the amount of leukotriene required to cause the disease, and the species of the mammal involved. As will be appreciated by those skilled in the art, the success of treating a mammal suffering from or susceptible to dermatoses characterized by an excessive release of leukotriene with a compound of Formula I will be measured by the regression or prevention of the symptoms of the condition.

Assays

Assay 1

The effectiveness of compounds of Formula I to inhibit the binding of tritiated $LTB_4$ to guinea pig lung membranes was determined as follows.

[$^3$H]-$LTB_4$ Radioligand Binding Assay in Guinea Pig Lung Membranes

[$^3$H]-$LTB_4$ (196–200 Ci/mmole) was purchased from New England Nuclear (Boston, Mass.). All other materials were purchased from Sigma (St. Louis, Mo.). Incubations (555 mL) were performed in polypropylene minitubes for 45 minutes at 30° C. and contained 25 mg of guinea pig lung membrane protein (Silbaugh, et al., *European Journal of Pharmacology*, 223 (1992) 57–64) in a buffer containing 25 mM MOPS, 10 mM $MgCl_2$, 10 mM $CaCl_2$, pH 6.5, approximately 140 pM [$^3$H]-$LTB_4$, and displacing ligand or vehicle (0.1% DMSO in 1 mM sodium carbonate, final concentration) as appropriate. The binding reaction was terminated by the addition of 1 mL ice cold wash buffer (25 mM Tris-HCl, pH 7.5) followed immediately by vacuum filtration over Whatman GF/C glass fiber filters using a Brandel (Gaithersburg, Md.) 48 place harvester. The filters were washed three times with 1 mL of wash buffer. Retained radioactivity was determined by liquid scintillation counting at 50% counting efficiency using Ready Protein Plus cocktail (Beckman, Fullerton, Calif.). Nondisplaceable binding was determined in the presence of 1 mM $LTB_4$ and was usually less than 10% of total binding. Data were analyzed using linear regression analysis of log-logit plots of the values between 10% and 90% of control binding to calculate $IC_{50}$s and slope factors (pseudo-Hill coefficients). $IC_{50}$ values thus obtained were corrected for radioligand concentration (Cheng and Prusoff, *Biochem. Pharmacol.*, 22, 3099 (1973)) to calculate $K_i$ values. pKi is the mean –log $K_i$ for n experiments.

Compounds of the instant invention tested in the above assay were found to have a pKi of between 7 and 11.

The ability of a compound of formula I to be an effective drug treatment for dermatoses can be evaluated in an irritant-induced model in either mice, guinea pigs or monkeys (Fretland et al., *Inflammation*, 19, 333–46, 1995).

Assay 2

Phorbol-12-myristate-13-acetate (PMA) in 0.1 ml DMSO is applied to the dorsal surface of the ear (20 μg for mice, 100 μg for guinea pigs and 200 μg for each monkey). Vehicle is layered on the contralateral ear. Eighteen hours after applying the irritant to mice and guinea pigs, the animals are killed by $CO_2$ asphyxiation, the ears extirpated and weighed to determine the amount of edema.

Neutrophil infiltration into the tissue can be measured by histological examination and/or analysis of the content of myeloperoxidase (MPO), a neutrophil marker enzyme. The latter is done by mincing the ears and then homogenizing them in hexadecyltrimethylammonium bromide detergent, sonicating and finally subjecting the material to a freeze-thaw cycle. After centrifuging the debris, MPO activity is assayed spectrophotometrically by determining the decomposition of peroxide using o-dianisidine as the hydrogen donor. Tissues are prepared in buffered formalin, embedded in paraffin, sectioned and stained with hematoxylin-eosin.

A compound of formula I is given either topically by coapplying with PMA or by gavage in 0.5% methylcellulose at 30 minutes before and again 90 minutes after PMA application. Dose-response effects are obtained by dividing the mice or guinea pigs into 4 experimental groups of 10 animals each. For topical treatment, 0.1 ml of either vehicle, 0.5, 1.0, or 2.0% (w/v) of a compound of formula I is applied to the ear. Corresponding groups for oral drug treatment are vehicle, 10, 25 and 50 mg/kg of a compound of formula I.

Epidermal inflammation in monkeys is measured by determining daily the ear thickness at identical anatomical loci with an electronic micrometer for 2 weeks. In the absence of an inhibitor, maximum response occurs at 4–6 days. Topical application of the compound to monkeys is carried out by coapplying with PMA but oral dosage is done by administering 10 ml of compounds in 0.5% methylcellulose to animals that are lightly anesthetized and chaired just after applying PMA to the ear.

Dose-response effects are obtained by dividing the animals into 4 experimental groups, each containing 4 monkeys. The doses of vehicle or a compound of formula I for topical and oral treatment are the same as those used on the smaller animal species.

For clinical studies, a compound of formula I can be tested in a double-blind, placebo controlled, crossover study in a manner similar to that used for evaluating other drugs (Swoden et al. *Lancet*, 338, 137–40, 1991; Sheehan, et al, *Lancet*, 340, 13–7, 1992).

Assay 3

One-half of patients with moderate to severe atopic dermatitis are treated for eight weeks with the drug and then, after a 4-week wash-out period, are treated for another eight weeks with a placebo. The other half of the patients are treated in reverse order. Subjects are orally administered 3 mg/kg of a compound of formula I or the placebo once a day. Patents are assessed every two weeks by measuring disease activity, extent of disease, loss of sleep and amount of itching, and topical steroid use.

For disease activity, six clinical features (erythema, purulence, excoriation or crusting, dryness or scaling, cracking or fissuring, and lichenification) are graded at six defined body sites (head and neck, mid-upper to mid-lower of both arms, anterior and posterior trunk, both hands, mid-thigh to mid-calf of both legs, and both feet) on a scale of 0 (none) to 3 (severe). Maximum total disease activity is 108. The extent of disease is measured in each defined area by estimating whether none, a third, two-thirds, or all of the area is affected. Severity of symptoms of itch and loss of sleep during the preceding two weeks is rated by the patient on a visual analogue scale (0–100 mm). Patients can continue with any topical steroid treatment that they had been using before entry in the study but the amount of drug needed by patient during each two week analysis period is noted. Comparisons of results between a compound of formula I and placebo treatments are made by standard statistical tests.

The therapeutic and prophylactic treatments provided by this invention are practiced by administering to a mammal in need thereof a dose of a compound of formula I or a pharmaceutically acceptable salt or solvate thereof, that is effective to inhibit or treat dermatoses such as atopic dermatitis, contact dermatitis, bullous pemphgoid urticaria diseases, potyriasis rubra pilaris and dyshidrosis.

The term "inhibit" includes its generally accepted meaning which includes prohibiting, preventing, restraining and slowing, stopping or reversing progression, severity or a resultant symptom. As such, the present method includes both medical therapeutic and/or prophylactic administration as appropriate.

While it is possible to administer a compound employed in the methods of this invention directly without any formulation, the compounds are usually administered in the form of pharmaceutical formulation comprising a pharmaceutically acceptable excipient and at least one active ingredient (the compound of the present invention). The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 0.01 to 90% by weight of the active compound in a suitable base, soft and hard gelatin capsules, suppositories, injectable solutions and suspensions in physiologically acceptable media, and sterile packaged powders adsorbed onto a support material for making injectable solutions. Such formulations are prepared in a manner well known in the pharmaceutical art and comprise at least one active compound. See, e.g., REMINGTON'S PHARMACEUTICAL SCIENCES, (16th ed. 1980).

In making the formulations employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, tragacanth, gelatin, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For topical administration, a compound of this invention ideally can be admixed with any variety of excipients in order to form a viscous liquid or cream-like preparation.

For oral administration, a compound of this invention ideally can be admixed with carriers and diluents and molded into tablets or enclosed in gelatin capsules.

In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention include capsules, tablets and topical preparations such as creams and ointments. Especially preferred are creams and ointments.

The therapeutic and prophylactic treatments provided by this invention are practiced by administering to a mammal in need thereof a dose of a compound of formula I or a pharmaceutically acceptable salt or solvate thereof that is effective to inhibit or treat dermatoses.

Advantageously for this purpose, formulations may be provided in unit dosage form, preferably each dosage unit containing from about 5 to about 500 mg (from about 5 to 50 mg in the case of parenteral or inhalation administration, and from about 25 to 500 mg in the case of oral or rectal administration) of a compound of Formula I. Dosages from about 0.5 to about 300 mg/kg per day, preferably 0.5 to 20 mg/kg, of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The specific dose of a compound administered according to this invention to obtain therapeutic or prophylactic effects will, of course, be determined by the particular circumstances surrounding the case, including, for example, the route of administration the age, weight and response of the individual patient, the condition being treated and the severity of the patient's symptoms.

In general, the compounds of the invention are most desirably administered at a concentration that will generally afford effective results without causing any serious side effects and can be administered either as a single unit dose, or if desired, the dosage may be divided into convenient subunits administered at suitable times throughout the day.

While all of the compounds illustrated above exemplify $LTB_4$ inhibition activity in vitro, we have also discovered that compounds bearing a single acidic group ($R_6$) are considerably more orally bioactive when administered to mammals compared with those compounds bearing two such acidic groups. Thus, a preferred embodiment when administering compounds of Formula I orally to mammals comprises administering compounds bearing a single acidic $R_6$ functionality.

The following formulation examples may employ as active compounds any of the compounds of this invention. The examples are illustrative only and are not intended to limit the scope of the invention in any way.

Formulation 1

Hard gelatin capsules are prepared using the following ingredients:

| | Quantity (mg/capsule) |
|---|---|
| 3-(2-(3-(2-Ethyl-4-(4-fluorophenyl)-5-hydroxy-phenoxy)propoxy)-6-(4-carboxyphenoxy)phenyl)-propanoic acid | 250 |
| Starch | 200 |
| Magnesium stearate | 10 |

The above ingredients are mixed and filled into hard gelatin capsules in 460 mg quantities.

Formulation 2

A tablet is prepared using the ingredients below:

| | Quantity (mg/tablet) |
|---|---|
| 1-(4-(Carboxymethoxy)phenyl)-1-(1H-tetrazol-5-yl)-6-(2-ethyl-4-(4-fluorophenyl)-5-hydroxyphenoxy)-hexane | 250 |
| Cellulose, microcrystalline | 400 |
| Silicon dioxide, fumed | 10 |
| Magnesium stearate | 5 |

The components are blended and compressed to form tablets each weighing 665 mg.

Formulation 3

An aerosol solution is prepared containing the following components:

| | Weight % |
|---|---|
| 3-[4-[7-Carboxy-9-oxo-3-[3-[2-ethyl-4-(4-fluorophenyl)-5-hydroxyphenoxy]propoxy]-9H-xanthene]]propanoic acid | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled to −30° C. and transferred to a filling device. The required amount is then fed to a container and further filled with the pre-mixed propellants 12 and 114 by means of the cold-filled method or pressure-filled method. The valve units are then fitted to the container.

Formulation 4

Tablets each containing 60 mg of active ingredient are made up as follows:

| | |
|---|---|
| 2-[2-Propyl-3-[3-[2-ethyl-5-hydroxy-4-(4-fluorophenyl)-phenoxy]propoxy]phenoxy]benzoic acid sodium salt | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| | |
|---|---|
| 5-[3-[2-(1-Carboxy)ethyl]-4-[3-[2-ethyl-4-(4-fluorophenyl)-5-hydroxyphenoxy]propoxy]phenyl]-4-pentynoic acid | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient are made as follows:

| | |
|---|---|
| 33-(2-(3-(2-Ethyl-4-(4-fluorophenyl)-5-hydroxyphenoxy)propoxy)-6-(4-carboxyphenoxy)phenyl)propanoic acid | 250 |
| Unsaturated or saturated fatty acid glycerides to | 2,000 mg |

The active ingredient is passed through a No. 60 mesh U.S. sieve and suspended in the fatty acid glycerides previously melted using the minimum heat necessary. The mixture is then poured into a suppository mold of nominal 2 g capacity and allowed to cool.

Formulation 7

Suspensions each containing 50 mg of medicament per 5 mL dose are made as follows:

| | |
|---|---|
| 2-[2-Propyl-3-[3-[2-ethyl-4-(4-fluorophenyl)-5-hydroxy-phenoxy]propoxy]phenoxy]benzoic acid | 50 mg |
| Sodium carboxymethyl cellulose | 50 mg |
| Sugar | 1 g |
| Methyl paraben | 0.05 mg |
| Propyl paraben | 0.03 mg |
| Flavor | q.v. |
| Color | q.v. |
| Purified water to | 5 mL |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

Formulation 8

An intravenous formulation may be prepared as follows:

| | |
|---|---|
| 2-[2-propyl-3-[3-[2-ethyl-4-(4-fluorophenyl)-5-hydroxy-phenoxy]propoxy]phenoxy]benzoic acid | 100 mg |
| Isotonic saline | 1,000 ml |

The solution of the above ingredients generally is administered intravenously to a subject at a rate of 1 ml per minute.

We claim:

1. A method for treating or inhibiting dermatoses in a mammal which comprises administering to a mammal in need thereof an effective amount of a compound of the formula I

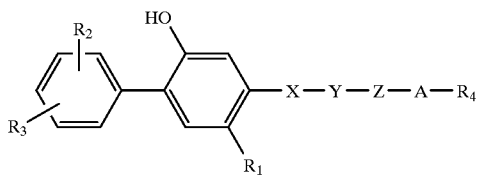

wherein:
$R_1$ is $C_1$–$C_5$ alkyl, $C_2$–$C_5$ alkenyl, $C_2$–$C_5$ alkynyl, $C_1$–$C_4$ alkoxy, ($C_1$–$C_4$ alkyl)thio, halo, or $R_2$-substituted phenyl;

each $R_2$ and $R_3$ are each independently hydrogen, halo, hydroxy, $C_1$–$C_4$alkyl, $C_1$–$C_4$alkoxy, ($C_1$–$C_4$ alkyl)—S(O)$_q$—, trifluoromethyl, or di-($C_1$–$C_3$ alkyl)amino;

X is —O—, —S—, —C(=O), or —CH$_2$—;
Y is —O— or —CH$_2$—;
or when taken together, —X—Y— is —CH=CH— or

Z is a straight or branched chain $C_1$–$C_{10}$ alkylidenyl;
A is a bond, —O—, —S—, —CH=CH—, or —CR$_a$R$_b$—, where R$_a$ and R$_b$ are each independently hydrogen, $C_1$–$C_5$ alkyl, or $R_7$-substituted phenyl, or when taken together with the carbon atom to which they are attached form a $C_4$–$C_8$ cycloalkyl ring;

$R_4$ is $R_6$,

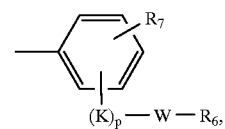

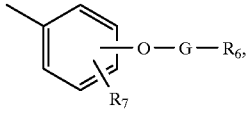

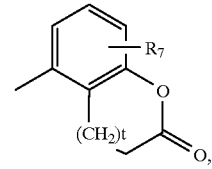

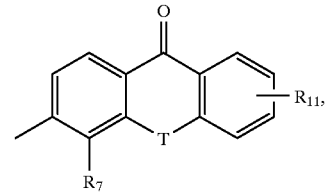

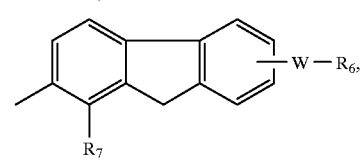

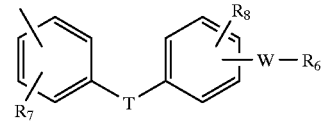

where,
each $R_6$ is independently —COOH, 5-tetrazolyl, —CON(R$_9$)$_2$, or —CONHSO$_2$R$_{10}$;

each $R_7$ is hydrogen, $C_1$–$C_4$ alkyl, $C_2$–$C_5$ alkenyl, $C_2$–$C_5$ alkynyl, benzyl, methoxy, —W—R$_6$, —T—G—R$_6$, ($C_1$–$C_4$ alkyl)—T—($C_1$–$C_4$ alkylidenyl)—O—, or hydroxy;

$R_8$ is hydrogen or halo;

each $R_9$ is independently hydrogen, phenyl, or $C_1$–$C_4$ alkyl, or when taken together with the nitrogen atom form a morpholino, piperidino, piperazino, or pyrrolidino group;

$R_{10}$ is $C_1$–$C_4$ alkyl or phenyl;
$R_{11}$ is $R_2$, —W—R$_6$, or —T—G—R$_6$;
each W is a bond or straight or branched chain divalent hydrocarbyl radical of one to eight carbon atoms;
each G is a straight or branched chain divalent hydrocarbyl radical of one to eight carbon atoms;
each T is a bond, —CH$_2$—, —O—, —NH—, —NHCO—, —C(=O)—, or —S(O)$_q$—;
K is —C(=O)— or —CH(OH)—;
each q is independently 0, 1, or 2;
p is 0 or 1; and
t is 0 or 1;
provided when X is —O— or —S—, Y is not —O—;
provided when A is —O— or —S—, $R_4$ is not $R_6$;

provided when A is —O— or —S— and Z is a bond, Y is not —O—; and provided W is not a bond when p is 0;

or a pharmaceutically acceptable salt or solvate thereof.

2. The method as claimed in claim 1 employing a compound of the formula

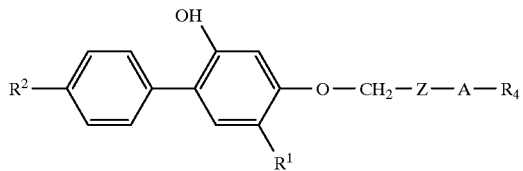

or a pharmaceutically acceptable salt or solvate thereof.

3. The method as claimed in claim 2 employing 2-[2-propyl-3-[3-[2-ethyl-4-(4-fluorophenyl)-5-hydroxyphenoxy]propoxy]phenoxy]benzoic acid or a pharmaceutically acceptable salt or solvate thereof.

4. The method as claimed in claim 2 employing 3-(2-(3-(2-ethyl-4-(4-fluorophenyl)-5-hydroxyphenoxy)propoxy)-6-(4-carboxy-phenoxy)phenyl)propionic acid or a pharmaceutically acceptable salt or solvate thereof.

5. The method as claimed in claim 2 employing 1-(4-(carboxy-methoxy)phenyl)-1-(1H-tetrazol-5-yl)-6-(2-ethyl-4-(4-fluorophenyl)-5-hydroxyphenoxy)hexane or a pharmaceutically acceptable salt or solvate thereof.

6. The method as claimed in claim 2 employing 3-[4-[7-carboxy-9-oxo-3-[3-[2-ethyl-4-(4-fluorophenyl)-5-hydroxyphenoxy]-propoxy]-9H-xanthene]]propanoic acid or a pharmaceutically acceptable salt or solvate thereof.

7. The method as claimed in claim 2 employing 5-[3-[2-(1-carboxy)-ethyl]-4-[3-[2-ethyl-4-(4-fluorophenyl)-5-hydroxyphenoxy]-propoxy]phenyl]-4-pentynoic acid or a pharmaceutically acceptable salt or solvate thereof.

8. The method as claimed in any one of claims 1 to 8 in which the mammal is a human.

9. The method as claimed in any one of claims 1 to 7 in which the dermatoses is selected from the group consisting of atopic dermatitis, contact dermatitis, bullous pemphigoid, urticaria diseases, petyriasis rubra pilaris and dyshedrosis.

* * * * *

UNITED STATES PATENT AND TRADEMARK OFFICE
CERTIFICATE OF CORRECTION

PATENT NO.     :   5,914,340

DATED          :   June 22, 1999

INVENTOR(S)    :   Jerome H. Fleisch, William T. Jackson and
                   Jason S. Sawyer It is certified that an error appears in the above-identified patent and that said Letters Patent is hereby corrected as shown below:

Column 1, line 40, the word "form" should read --from--.

Column 1, line 45, the word "order" should read --older--.

Column 4, line 55, after the word as, the formula "-CH=CH-" should read -- -CH=Ch$_2$-.

Column 6, line 21, the formula "-T-C-COOH" should read -- -T-G-COOH--.

Signed and Sealed this

Thirtieth Day of May, 2000

Attest:

Q. TODD DICKINSON

*Attesting Officer*     *Director of Patents and Trademarks*